United States Patent [19]

Elishewitz et al.

[11] Patent Number: 5,122,234
[45] Date of Patent: Jun. 16, 1992

[54] PREPARATION OF PHENOL HAVING IMPROVED CLARITY WHEN DISPERSED IN WATER

[75] Inventors: Saul L. Elishewitz, Philadelphia; Clifford M. Gilpin, III, Churchville; Gerald E. Hollenbach, Feasterville, all of Pa.; John J. Santarsiero, II, Mt. Laurel, N.J.; William J. Moffatt, Flossmoor, Ill.; David B. Lebowitz, Cherry Hill, N.J.; Dodd S. Smith, Schweiksville, Pa.; Larry B. Wolf, Colonial Heights, Va.

[73] Assignee: Allied-Signal Inc., Morristownship, N.J.

[21] Appl. No.: 650,253

[22] Filed: Feb. 4, 1991

Related U.S. Application Data

[63] Continuation-in-part of Ser. No. 443,063, Nov. 28, 1989, abandoned, which is a continuation of Ser. No. 927,904, Nov. 6, 1986, abandoned.

[51] Int. Cl.⁵ .................... B01D 3/42; C07C 37/74
[52] U.S. Cl. ........................... 203/1; 203/79; 203/96; 203/DIG. 18; 203/DIG. 19; 568/754
[58] Field of Search .............. 203/92, 93, 96, 97, 203/79, DIG. 19, 99, 14, 1, 85, DIG. 18; 568/754, 749

[56] References Cited

U.S. PATENT DOCUMENTS

| | | | |
|---|---|---|---|
| 3,212,997 | 10/1965 | Walker | 203/2 |
| 3,896,006 | 7/1975 | Cooke | 568/754 |
| 3,905,874 | 9/1975 | Griffin et al. | 203/1 |

FOREIGN PATENT DOCUMENTS

| | | | |
|---|---|---|---|
| 865677 | 4/1961 | United Kingdom . | |
| 873604 | 7/1961 | United Kingdom | 568/754 |

Primary Examiner—Wilbur Bascomb, Jr.

[57] ABSTRACT

This invention is a continuous process for preparing phenol having improved clarity when dispersed in water. The phenol is prepared from crude phenol being the product of decomposition of cumene hydroperoxide and having previously been distilled to remove large portions of acetone, cumene and alphamethyl styrene. The continuous process requires a) introducing the crude phenol as a feed to a fractional distillation column, b) heating the bottoms of the fractional distillation column to vaporize the phenol and lower boiling components of the crude phenol, c) removing those components of the crude phenol boiling higher than phenol from the bottom of the distillation column, d) removing substantially dry liquid phenol product with improved clarity from the distillation column at a point at least one theoretical stage from the top of the column, e) adding water to the top of the fractional distillation column in a sufficient amount to improve the clarity of the phenol product, f) removing a condensed liquid phenol-water mixture containing impurities overhead from the top of the fractional distillation column, and g) returning a portion of the phenol-water mixture to the top of the fractional distillation column as reflux.

13 Claims, 2 Drawing Sheets

PREPARATION OF PHENOL HAVING IMPROVED CLARITY WHEN DISPERSED IN WATER

This is a continuation-in-part of copending U.S. Ser. No. 443,063 filed Nov. 28, 1989, now abandoned which was a continuation of U.S. Ser. No. 927,904 filed Nov. 6, 1986, now abandoned.

BACKGROUND OF THE INVENTION

This invention relates to a method to prepare phenol from the products of decomposition (cleavage) of cumene hydroperoxide. Various decomposition product components, such as acetone, unreacted cumene, and alpha methyl styrene are removed by traditional distillation, leaving crude phenol. The method of this invention improves clarity of the resultant phenol, when dispersed in water.

The process for preparing cumene hydroperoxide for use as precursor feed for this invention can be by any of the known prior art processes, such as that described in U.S. Pat. No. 3,907,901, hereby incorporated by reference. Various distillation methods to separate the various components resulting from the cleavage of cumene hydroperoxide may be used, such as the teaching, which includes a method of treating crude phenol with alkaline hydrogen peroxide to remove mesityl oxide and its precursor impurities, described in U.S. Pat. No. 2,971,893, hereby incorporated by reference. Also see column 1 of U.S. Pat. No. 4,532,012 hereby incorporated by reference, in toto.

The test for clarity in water of phenol has been called the water light transmission (WLT) or water solubility test, described at column 1, lines 52-59, of U.S. Pat. No. 2,910,511, hereby incorporated by reference in toto.

The preferred prior art method to prepare crude phenol by fractional distillation from the product of decomposition of cumene hydroperoxide is shown in FIG. 1. Cumene, fresh and recycled, is fed through line 20 to an oxidizer 21 to form cumene hydroperoxide (CHP). CHP is fed to a decomposer 22 wherein CHP cleavage products result and some unreacted cumene is recycled. The remaining products are stored in crude storage 23 then fractionally distilled in a series of columns 24, 25, 26 and 27 as shown. The first distillation 24 removes acetone for further refining and sale. The second distillation 25 removes cumene for recycle to oxidizer feed. The third distillation 26 removes alphamethyl styrene (AMS) for further processing. The final column 27 produces phenol product overhead and takes organic residue from the bottom. This invention involves operation of the final phenol distillation column.

By external reflux ratio herein is meant overhead condensed liquid returned to the column top (reflux) flow rate divided by liquid overhead take-off flow rate.

SUMMARY OF THE INVENTION

This invention is a continuous process for preparing phenol having improved clarity when dispersed in water. The phenol is prepared from crude phenol being the product of decomposition of cumene hydroperoxide and having previously been distilled to remove large portions of acetone, cumene and alphamethyl styrene. The method of the invention comprises (a) continuously introducing said crude phenol as a feed to a fractional distillation column said feed being in the lower one third of the column, said column having many theoretical distillation stages including a bottom of said column which contains bottoms and having a condenser for overhead vapors, (b) continuously heating the bottoms of said fractional distillation column to vaporize the phenol and lower boiling components of said crude phenol, (c) continuously removing those components of said crude phenol boiling higher than phenol from the bottom of said distillation column, (d) continuously removing substantially dry liquid phenol product from said fractional distillation column in the upper one third of the column and at a point at least one theoretical stage from the top of said column, said phenol product having improved clarity when dispersed in water, (e) continuously adding water, in addition to water present in reflux to the column, to the top of said fractional distillation column, to prevent formation of dimers of alphamethyl styrene said alphamethyl styrene being present in small amounts in said crude phenol feed, in an amount sufficient to improve the clarity of said phenol product when dispersed in water, said clarity being not less than 93 percent light transmission as determined by an electrophotometer but not in an amount great enough to cause said phenol product to contain more than 0.1 percent water by weight, (f) continuously removing a condensed liquid phenol-water mixture containing impurities overhead from the top of said fractional distillation column, (g) continuously returning a portion of said phenol-water mixture to the top of said fractional distillation column as reflux, wherein said distillation column is substantially dry except for at most its top 5 trays provided that the product phenol take-off tray is one of the substantially dry trays below said excepted trays and wherein said phenol product may contain color formers such as methylbenzofuran.

It is preferred to feed the crude phenol of step (a) near or at the bottom of the distillation column. It is preferred to operate the distillation column at a pressure of between about 50 and 250 Torr column top pressure, and between about 100 and 400 Torr column bottom pressure, a top temperature between about 60° and 145° C., and bottom temperature between about 125° and 170° C. It is also preferred to operate the distillation column at a feed flow rate of between about 6,135 and 20,865 kilograms per hour (1,500 and 5,100 gallons per hour) and a phenol product flow of between about 2,045 and 19,430 kilograms per hour (500 and 4,750 gallons per hour). It is preferred to operate the distillation column at an external reflux ratio of between about 3 and 200 and even more preferably between about 9 and 90. The preferred overhead take off flow rate from the distillation column is between about 123 and 2,864 kilograms per hour (30 and 700 gallons per hour). It is preferred to add water to the top of the distillation column at a flow rate of between about 0.01 to 0.9 times the flow rate of the overhead flow rate in step (f). It is preferred to add water to the top of the distillation column at a flow rate of between 11 and 245 kilograms per hour (3 and 60 gallons per hour). The preferred feed to the distillation column is in the lower one third of the column and the phenol product is drawn off in the upper one third of the column.

Optionally, the flow rate of the phenol product removed can be controlled by controlling the flow rate of the phenol product described in step d) by means of a ratio controller which senses the flow rate of the feed described in step (a) and the flow rate of the phenol product of step (d) and regulates the flow of the phenol product to maintain a constant preset ratio. The preferred ratio is between about 3 and 1.05 to 1, feed flow to product flow. It is preferred that the distillation column contain between about 7 and 35 theoretical stages, or between about 15 and 75 actual distillation trays.

In this invention, the distillation column is dry except for the top five trays. The only source of water is the water added to the top of the column which is in addition to the water recycling in the reflux. Substantially all of this recycling water was also originally added to the top of column. Both the feed and the phenol product taken off in a side stream high in the column are substantially dry.

This invention is distinguished from the prior art directed to removing color forming impurities, in that the phenol product may contain color formers such as methylbenzofuran (MBF) and/or acetol (also called hydroxyacetone). In fact, as shown in Table 2, the phenol product of this invention does contain MBF and acetol in sufficient quantities to cause color by the prior art tests for color. For example see Example 1 of G.B. 865,677.

DESCRIPTION OF THE PREFERRED EMBODIMENT

Figure 1:
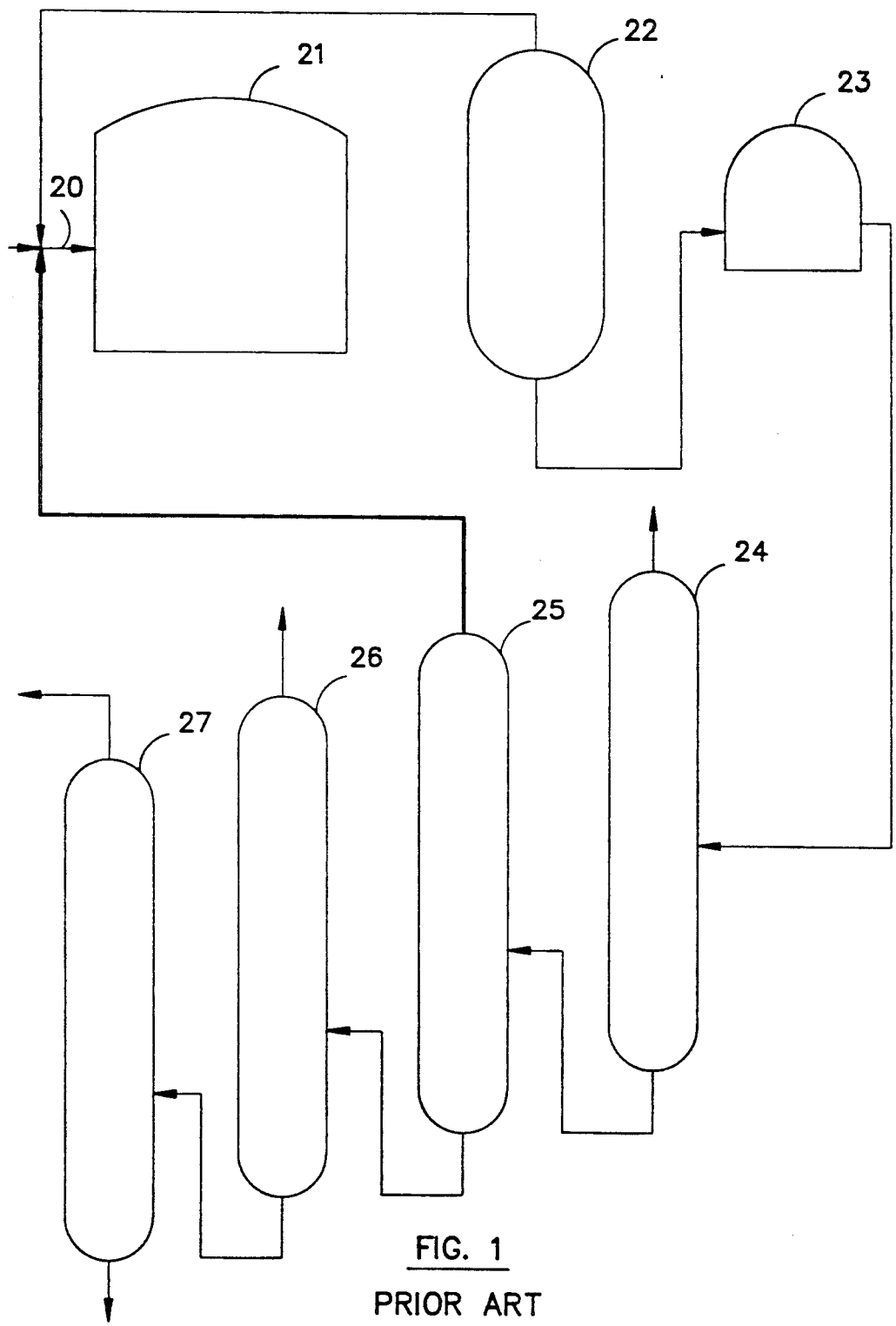
FIG. 1, labeled Prior Art is a schematic showing the prior flow diagram for producing phenol from cumene, and is described above.
Figure 2:
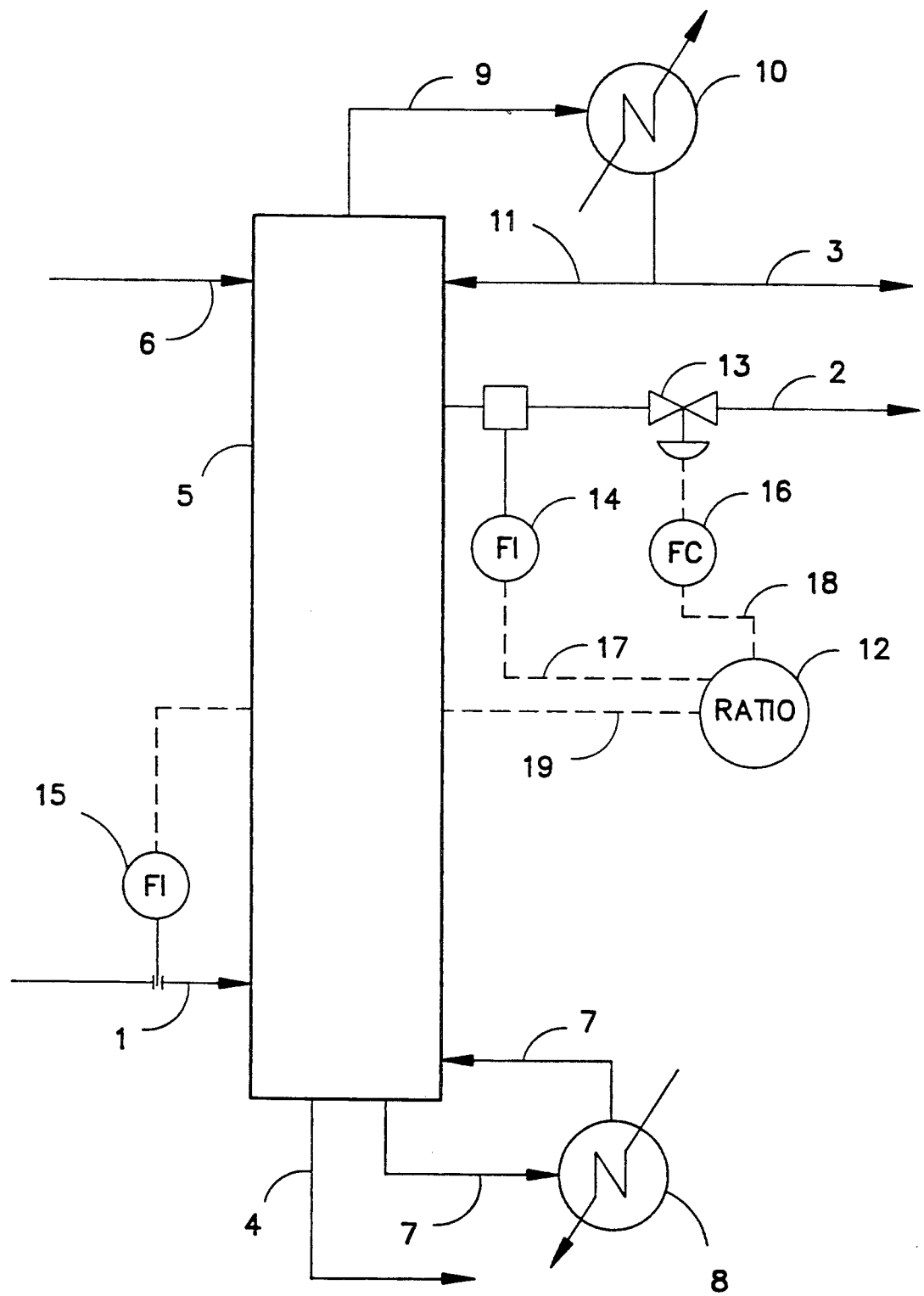
FIG. 2 is a schematic of the final phenol distillation column, modified to operation by means of this invention.

Operation of the phenol distillation by means of this invention is shown in FIG. 2. Crude phenol from the previous AMS distillation column is fed to column 5 through line 1, where it is distilled by heating by boiler 8 through lines 7 in the column bottom, to distill purified phenol product upward to be removed as a side cut near the column top, line 2. A pasteurizing overhead cut is taken from line 3, a portion of the overhead vapors being condensed by condenser 10 is in overhead line 9. This overhead cut can be returned to the upstream continuous distillation system such as the cumene distillation column or sent to storage for further purification such as by batch distillation. Reflux (condensed liquid overhead after the pasteurizing cut is taken off) from condenser 10 is returned to column 5 through line 11. A small amount of water is added to the top of column 5 through line 6. Phenol and organic residues, including acetophenone, are removed from the column 5 bottom through line 4.

Optionally, flow of phenol product through line 2 can be regulated by means of a flow controller 16 which is in turn controlled by ratio controller 12, which senses, through electronic or pneumatic means lines 19 and 17 flow in the feed line 1 and product line 2. Flow indicators 14 and 15 indicate the flow in their respective lines 2 and 1. Ratio controller 12 controls control valve 13 through line 18 to flow controller 16 to keep the flow of product in line 2 at a preset ratio to flow of feed in line 1.

EXAMPLE OF A PREFERRED EMBODIMENT

For a typical feed composition as given in Table 1, following are the preferred operating conditions and resulting composition of bottoms, product and overhead streams, shown in Tables 2 to 4. The values shown are the average of several days, runs.

PREFERRED OPERATING CONDITIONS

The following conditions are the preferred method of operating two actual phenol distillation columns, each configured as shown in FIG. 2. Column 1 has 35 actual distillation trays, column 2 has 32 actual distillation trays. Product is drawn off at tray 30 in column 1, tray 28 in column 2. Although water injection ("added to top column") is shown at 30 gallons per hour, and is preferred, the data for composition of the streams in Tables 2 to 4 was at 60 gallons per hour.

| | Values | | | |
|---|---|---|---|---|
| | Column 1 | | Column 2 | |
| Condition | gph | kg/hr (1) | gph | kg/hr (1) |
| Flows. | | | | |
| Feed | 2533 | 10362 | 4040(2) | 16527 |
| Product | 1724 | 7053 | 3643 | 14903 |
| Overhead Take-off | 121 | 485 | 526 | 2104 |
| Water Added Top Column | 30 | 114 | 30 | 114 |
| Bottoms (3) | 392 | 1604 | 1404 | 5777 |
| Reflux(4) | 2517 | 10300 | 4540 | 18573 |
| Rate, pph | 5224 | 2370 | 13324 | 6045 |
| Steam to Boiler | | | | |
| Ratios | | | | |
| Product: Feed | 0.68 | | 0.9 | |
| Water: Overhead Take-off | 0.25 | | 0.057 | |
| Temperatures. °C. | | | | |
| Top | 122 | | 131 | |
| Tray 28 | 140 | | 139 | |
| Tray 15 | | | 150 | |
| Bottom | 157 | | 159 | |
| Pressure. Torr | | | | |
| Top | 160 | | 218 | |
| Bottom | 306 | | 356 | |

(1) Calculated from meter rates
(2) Accuracy questionable, meter may be reading low by a factor of 1.2 to 1.3.
(3) Accuracy questionable.
(4) Calculated from heat balance.

The phenol product stream had 96.4 percent and 95.6 percent water light transmission in columns 1 and 2 respectively by the following test method.

PROCEDURE - WATER LIGHT TRANSMISSION TEST (1) Into two 100-milliliter cylinders, measure 75 milliliters of distilled water at 25° C. Pipet 5 milliliters of phenol sample, at 55° to 60° C., into one of the cylinders. Stopper, shake vigorously and allow to stand for ten minutes at 25° C.

(2) Compare the clarity of the sample solution with that of the distilled water. Do this by looking through the sides of the cylinders which are held about three feet from a window in such a manner that the line of sight is against the vertical dark surface below the sill. The light should be north light and sunlight glare must be avoided. Artificial light should come from a "daylight" lamp in such a manner as to simulate the above condition.

(3) Remove the stopper from the cylinder, tilt the cylinder slightly at various angles and observe the surface of the liquid for an oil separation.

(4) If the sample solution is not clear and when the degree of cloudiness is to be determined by a photometer, transfer 60 milliliters at 25° C., to the absorption cell and determine the percent light transmission, using 60 milliliters of distilled water in the reference cell.

(5a) If the sample solution is clear and no oil is observed on the surface, report as "clear at 25° C.".

(5b) If the sample solution is cloudy and/or shown any separated oil, report the degree of cloudiness as "slightly-hazy - hazy - cloudy - opaque" and the oil present as "trace" or "oil present" dependent upon the amount.

(5c) If the degree of cloudiness was determined by the electrophotometer, report the percent light transmission. Less than 93 percent light transmission is not water clear.

DISCUSSION

Although not apparent at first, addition of a small amount of water to the top of a phenol distillation column appears to prevent formation of dimers of AMS, which destroy the light transmission or clarity of phenol mixed or dispersed in water, even in very small quantities. Other impurities also contribute to lack of clarity but these have not yet been identified. Note that clarity (transparent versus translucent) of the dispersed phenol in water is the phenomenon measured, not color. "Water clear" phenol is generally marketable product to industry in general. Previously, because the end user had to further process product that was not "water clear" phenol to make it suitable for the intended use, such product was not sold, but used for feed to a hydrogenation process.

By use of water addition or injection to the top of the column, the pasteurizing overhead take-off is much more efficient, creating "water clear" side cut product phenol. The water injection permits less overhead take-off, thereby providing greater reflux flow to the column. Also the product phenol contains less AP, PPA and other residue because the increased reflux flow effect of the water injection drives these impurities down the column and out with the bottoms. Alternatively, using less water, less reflux still creates high percent transmission WLT test product "water clear" phenol with similar amounts of AP, PPA and other residue but at lower cost, due to reduced energy requirements, because less cooling for condensation of water required. Both alternatives are embodiments of this invention.

Table 7 shows an Acids Analysis of Phenol Columns, the data labeled "Invention" being for the same distillation column operating as described above i.e., with water, in addition to the water being recycled in the reflux, being added at the column top. Note that the only source of water present in the distillation column is by addition to the column top. The feed is dry. The data labeled "Prior Art" is from a column substantially the same in structure and operation, but operated under prior art conditions of no addition of water, other than in reflux, at the column top.

Table 7 clearly shows that by operating the column according to the method of this invention, i.e. by using added water (in addition to water in reflux) at the column top, acid content of the phenol product is more than halved. It is theorized that use of additional water, plus the water already in the reflux, at the column top in, at most, the top four theoretical stages or actual trays surprisingly takes acids overhead with the water and phenol, part of which is removed in the pasteurizing cut, see the very high acids content in the pasteurizing cut (Table 7), both in the water and in the phenol. (The pasteurizing cut comes from the operating column as one stream but separates into water and phenol in the laboratory before it can be analyzed.) Also the vacuum jet exhaust has a relatively high acids content. Note in Table 2 that the product of this invention is dry, has only 0.03% by weight water. So only the trays above the product draw-off tray could be wet. We believe this extra, additional water, by an as-yet unknown mechanism, surprisingly keeps the acids from refluxing back down onto or below the product take-off tray as evidenced in Table 7 (first column). We theorize the lack of acids prevents catalysis of the AMS into AMS dimers which, when present, cause poor light transmission of phenol dispersed in water, e.g., cause product phenol of the prior art process to fail the water light transmission test. We feel that without the extra, additional water in the column top in the process or this invention, the prior art process allowed the volatile acids to be condensed with the product phenol catalyzing any AMS also present to AMS dimer. Somehow the excess water in the column top of this invention holds the acids above the take-off tray for product phenol. These acids are then removed with pasteurizing cut instead of with product phenol.

COMPARATIVE EXAMPLE

To compare the effect of water addition (injection) to the top of column 1, it was operated as described above in "Preferred Operating Conditions" with feed composition of Table 1, except no water was injected. Table 5 shows the typical composition for the overhead stream and Table 6 shows the typical composition for the product stream with no water injection. The Bottoms Stream Composition is essentially the same. The clarity of the phenol in water was hazy to cloudy and the typical WLT tests ranged from 40 to 90 percent to various samples.

TABLE 1

| FEED STREAM COMPOSITION | |
|---|---|
| Component | Percent by Weight |
| Intermediate Boilers | 0.2 |
| Phenol | 95.0 |
| Alphamethylstyrene (AMS) | 0.1 |
| Acetophenone (AP) | 1.0 |
| AMS Dimers | 0.5 |
| Cumyl Phenol (CP) | 1.2 |
| Residue | 2.0 |
|  | 100.0 |

TABLE 2

| PRODUCT STREAM COMPOSITION | | |
|---|---|---|
| Component | Percent By Weight | Parts Per Million |
| Phenol (1) | 99.5109 | — |
| AMS | 0.0323 | 323 |
| AP | 0.1300 | 1300 |
| Water | 0.030 | — |
| Cumene | 0.0031 | 31 |
| Acetone | 0.0014 | 14 |
| Dimethylphenyl Carbinol (DMPC) | 0.0002 | 2 |

TABLE 2-continued
PRODUCT STREAM COMPOSITION

| Component | Percent By Weight | Parts Per Million |
|---|---|---|
| Mesityloxide (MO) | 0.0051 | 51 |
| Methylbenzofuran (MBF) | 0.0063 | 63 |
| Acetol | 0.1888 | 1888 |
| Phenylproprionaldehyde (PPA) | 0.0689 | 689 |
| Unknowns | 0.0230 | 230 |
| AMS Dimers | 0 | — |
| CP | 0 | |
| | 100.00 | |

(1) Phenol determined by (100-0.4891)

TABLE 3
OVERHEAD STREAM COMPOSITION

| Component | Percent By Weight | Parts Per Million |
|---|---|---|
| Phenol (1) | 72.72 | — |
| AMS | 0.2660 | 2660 |
| AP | 0.0066 | 66 |
| Water | 26.70 | — |
| Cumene | 0.0025 | 25 |
| Acetone | 0.0178 | 178 |
| DMPC | 0.0035 | 35 |
| MO | 0.0037 | 37 |
| MBF | 0.0044 | 44 |
| Acetol | 0.2257 | 2257 |
| PPA | 0.0038 | 38 |
| Unknowns | 0.0462 | 462 |
| AMS Dimers | 0 | |
| CP | 0 | |
| | 100.00 | |

(1) Phenol calculated (100-27.28) percent

TABLE 4
BOTTOMS STREAM COMPOSITION

| Component | Percent by Weight |
|---|---|
| Phenol | 80.0 |
| AP and Heavy Organics | 4.0 |
| AMS Dimers | 2.0 |
| CP | 0.8 |
| PPA | 0.6 |
| Residue | 12.6 |
| | 100.0 |

TABLE 5
OVERHEAD STREAM COMPOSITION (TYPICAL) (COMPARATIVE)

| Component | Percent By Weight | Parts Per Million |
|---|---|---|
| Acetone | 0.0012 | 12 |
| Mesityl Oxide | 0.006 | 60 |
| Cumene | 0.0027 | 27 |
| Acetol | 0.18 | 1840 |
| AMS | 0.03 | 300 |
| MBF | 0.0065 | 65 |
| AP | 0.014 | 140 |
| DMPC | 0 | 0 |
| Phenol | 99.2 | — |
| Water | 0.03 | 300 |
| CP | 0.007 | 70 |
| AMS Dimers | 0.02 | 200 |
| Other and Unknowns | 0.377 | |
| | 100.00 | |

TABLE 6
PRODUCT STREAM COMPOSITION (TYPICAL) (COMPARATIVE)

| Component | Percent By Weight | Parts Per Million |
|---|---|---|
| Phenol | 99.2 | — |
| AMS | 0.01 | 100 |
| AP | 0.11 | 1100 |
| Water | 0.03 | 300 |
| Cumene | 0.003 | 30 |
| Acetol | 0.2 | 2000 |
| DMPC | 0.002 | 20 |
| CP | 0.2 | 2000 |
| AMS Dimers | 0.02 | 250 |
| Others and Unknowns | 0.325 | |
| | 100.00 | |

TABLE 7
ACIDS ANALYSIS OF PHENOL COLUMNS ACID CONTENT (PPM)

| | Invention | | | | Prior Art |
|---|---|---|---|---|---|
| ACIDS | Product (1) | P. Cut Water (2) | P. Cut Phenol (3) | Jet (4) | Product (5) |
| Benzoic | ND[6] | ND | ND | ND | ND |
| Succinic | ND | ND | ND | ND | 4.00 |
| Maleic | ND | ND | ND | ND | ND |
| Sulfuric | 0.64 | 2.77 | 0.42 | 0.93 | 0.43 |
| Oxalic | ND | ND | ND | ND | ND |
| Lactic | 2.02 | ND | ND | ND | 11.64 |
| Formic | 3.88 | 321.55 | 123.50 | 56.45 | 4.35 |
| Acetic | 3.43 | 22.45 | 23.91 | 6.33 | 2.66 |
| Propionic | ND | ND | ND | ND | ND |
| Isobutyric | 2.73 | 4.56 | 6.30 | ND | 5.67 |
| TOTAL | 12.70 | 351.33 | 154.13 | 63.71 | 28.75 |

NOTES
(1) Phenol Column Product Composite of Three Samples
(2) Phenol Column Pasteurizing Cut. Water Layer. Composite of Three Samples
(3) Phenol Column Pasteurizing Cut. Phenol Layer. Composite of Three Samples
(4) Phenol Column Vacuum Jet Composite of Three Samples
(5) Phenol Column Composite of Three Samples
(6) ND = Not Detected

We claim:

1. The continuous process for preparing phenol having improved clarity when dispersed in water; said phenol prepared from crude phenol being the product of decomposition of cumene hydroperoxide and having previously been distilled to remove large portions of acetone, cumene and alphamethyl styrene, comprising a) continuously introducing said crude phenol as a feed to a fractional distillation column said feed being in the lower one third of the column, said column having many theoretical distillation stages including a bottom of said column which contains bottoms and having a condenser for overhead vapors, b) continuously heating the bottoms of said fractional distillation column to vaporize the phenol and lower boiling components of said crude phenol, c) continuously removing those components of said crude phenol boiling higher than phenol from the bottom of said distillation column, d) continuously removing substantially dry liquid phenol product from said fractional distillation column from a product phenol take-off tray in the upper one third of the column and at a point at least one theoretical stage from the top of said column, said phenol product having improved clarity when dispersed in water, e) continuously adding water, in addition to water present in reflux to the column, to the top of said fractional distillation column, to prevent formation of dimers of alphamethyl styrene said alphamethyl styrene being present in small amounts in said crude phenol feed, in an amount sufficient to improve the clarity of said phenol product when dispersed in water, said clarity being not less than 93 percent light transmission as determined by an electrophotometer but not in an amount enough to cause said phenol product to contain more than 0.1 percent water by weight, f) continuously removing a condensed liquid phenol-water mixture containing impurities overhead from the top of said fractional distillation column, g) continuously returning a portion of said phenol-water mixture to the top of said fractional distillation column as reflux, wherein said distillation column is substantially dry except for at most its top 5 trays provided that the product phenol take-off tray is one of the substantially dry trays below said excepted trays.

2. The method of claim 1 wherein the phenol feed of step a) is fed near or at the bottom of the distillation column.

3. The method of claim 1 wherein the distillation column operates at a pressure of between about 50 and 250 Torr column top pressure and between about 100 and 400 Torr column bottom pressure, a top temperature of between about 60° C. and 145° C., a bottom temperature of between about 125° and 170° C.

4. The method of claim 3 wherein the distillation column operates at a feed flow rate of between about 6,135 and 20,865 kilograms per hour (1,500 and 5,100 gallons per hour) and a phenol product flow of between about 2,045 and 19,430 kilograms per hour (500 and 4,750 gallons per hour).

5. The method of claim 3 wherein the distillation column operates at an external reflux ratio of between 3 and 200.

6. The method of claim 4 wherein the distillation column operates at an external reflux ratio of between about 9 and 90.

7. The method of claim 6 wherein the column operates at an overhead take off flow rate of between about 123 and 2,864 kilograms per hour (30 and 700 gallons per hour).

8. The method of claim 3 wherein the water is added to the top of the distillation column at a flow rate of between about 0.01 to 0.9 times the flow rate of the overhead flow rate in step f).

9. The method of claim 7 wherein the water is added to the top of the distillation column at a flow rate of between about 11 and 245 kilograms per hour (3 and 60 gallons per hour).

10. The process for preparing phenol having improved clarity when dispersed in water; said phenol prepared from crude phenol being the product of decomposition of cumene hydroperoxide and having previously been distilled to remove large portions of acetone, cumene and alphamethyl styrene, comprising a) introducing said phenol as a feed to a fractional distillation column said column having many theoretical distillation stages, having a condenser for overhead vapors, and including a bottom of said column which contains bottoms, b) heating the bottoms of said fractional distillation column to vaporize the phenol and lower boiling components of said crude phenol, c) removing those components of said crude phenol boiling higher than phenol from the bottom of said distillation column, d) removing substantially dry liquid phenol product from said fractional distillation column at a point at least one theoretical stage from the top of said column, said phenol product having improved clarity when dispersed in water, e) adding water to top of said fractional distillation column in an amount sufficient to improve the clarity when dispersed in water of said phenol product, but not in an amount great enough to cause said phenol product to contain more than 0.1 percent water by weight, f) removing a condensed liquid phenol-water mixture containing impurities overhead from the top of said fractional distillation column, g) returning a portion of said phenol-water mixture to the top of said fractional distillation column as reflux, h) controlling the flow rate of said phenol product removed as described in step d) by means of a ratio controller which senses the flow rate of the feed described in step a) and the flow rate of the phenol product of step d) and regulates the flow of said phenol product to maintain a constant preset ratio of feed flow to product flow.

11. The method of claim 10 wherein said ratio of step h) is between about 3.0 and 1.05 to 1, feed flow: product flow.

12. The method of claim 11 wherein said distillation column contains between about 7 and 35 theoretical stages.

13. The method of claim 11 wherein said distillation column contains between about 15 and 75 actual distillation trays.

* * * * *